(12) United States Patent
Henderson et al.

(10) Patent No.: US 6,665,555 B2
(45) Date of Patent: Dec. 16, 2003

(54) RADIOSURGERY METHODS THAT UTILIZE STEREOTACTIC METHODS TO PRECISELY DELIVER HIGH DOSAGES OF RADIATION ESPECIALLY TO THE SPINE

(75) Inventors: Fraser C. Henderson, Washington, DC (US); James Rodgers, Washington, DC (US); Azam Niroomand-Rad, Washington, DC (US); Kevin Cleary, Washington, DC (US); Anatoly Dritschilo, Washington, DC (US); Leon Der, Washington, DC (US)

(73) Assignee: Georgetown University School of Medicine, Washington, DC (US)

( * ) Notice: Subject to any disclaimer, the term of this patent is extended or adjusted under 35 U.S.C. 154(b) by 0 days.

(21) Appl. No.: 09/826,000

(22) Filed: Apr. 5, 2001

(65) Prior Publication Data

US 2002/0032378 A1 Mar. 14, 2002

Related U.S. Application Data

(60) Provisional application No. 60/194,589, filed on Apr. 5, 2000.

(51) Int. Cl.[7] .................................................. A61B 5/05
(52) U.S. Cl. ......................... 600/427; 128/899; 378/64; 378/65; 600/425; 600/473; 600/476; 600/1; 600/2; 600/3
(58) Field of Search ................................. 600/425, 427, 600/429, 473, 476, 160, 1, 2, 3; 359/462; 356/12; 128/898; 378/165, 62, 63, 64, 68, 4, 21, 41, 42; 606/130; 382/154

(56) References Cited

U.S. PATENT DOCUMENTS

| | | | | |
|---|---|---|---|---|
| 4,998,268 A | * | 3/1991 | Winter | 378/147 |
| 5,207,223 A | * | 5/1993 | Adler | 600/427 |
| 5,281,232 A | * | 1/1994 | Hamilton et al. | 600/429 |
| 5,339,812 A | * | 8/1994 | Hardy et al. | 600/429 |
| 5,458,125 A | | 10/1995 | Schweikard | 128/653 |
| 5,643,268 A | | 7/1997 | Vilsmeier et al. | 606/73 |
| 5,778,043 A | * | 7/1998 | Cosman | 378/206 |
| 5,815,547 A | * | 9/1998 | Shepherd et al. | 378/65 |
| 5,894,503 A | * | 4/1999 | Shepherd et al. | 250/505.1 |
| 6,143,003 A | * | 11/2000 | Cosman | 128/846 |
| 6,259,943 B1 | * | 7/2001 | Cosman et al. | 600/417 |
| 6,422,748 B1 | * | 7/2002 | Shepherd et al. | 250/505.1 |

* cited by examiner

Primary Examiner—Marvin M. Lateef
Assistant Examiner—Jeoyuh Lin
(74) Attorney, Agent, or Firm—Pillsbury Winthrop LLP

(57) ABSTRACT

A system for delivery of high dosage of radiation to a targeted spinal area is provided. This is accomplished by a system which provides for precise immobilization and positioning of the treated spinal area during dose planning and treatment via stereotactic radiosurgery. Advantages of the system include convenience to the patient, enhanced efficacy, and reduced risk of radiotoxicity to non-target tissues.

15 Claims, 7 Drawing Sheets

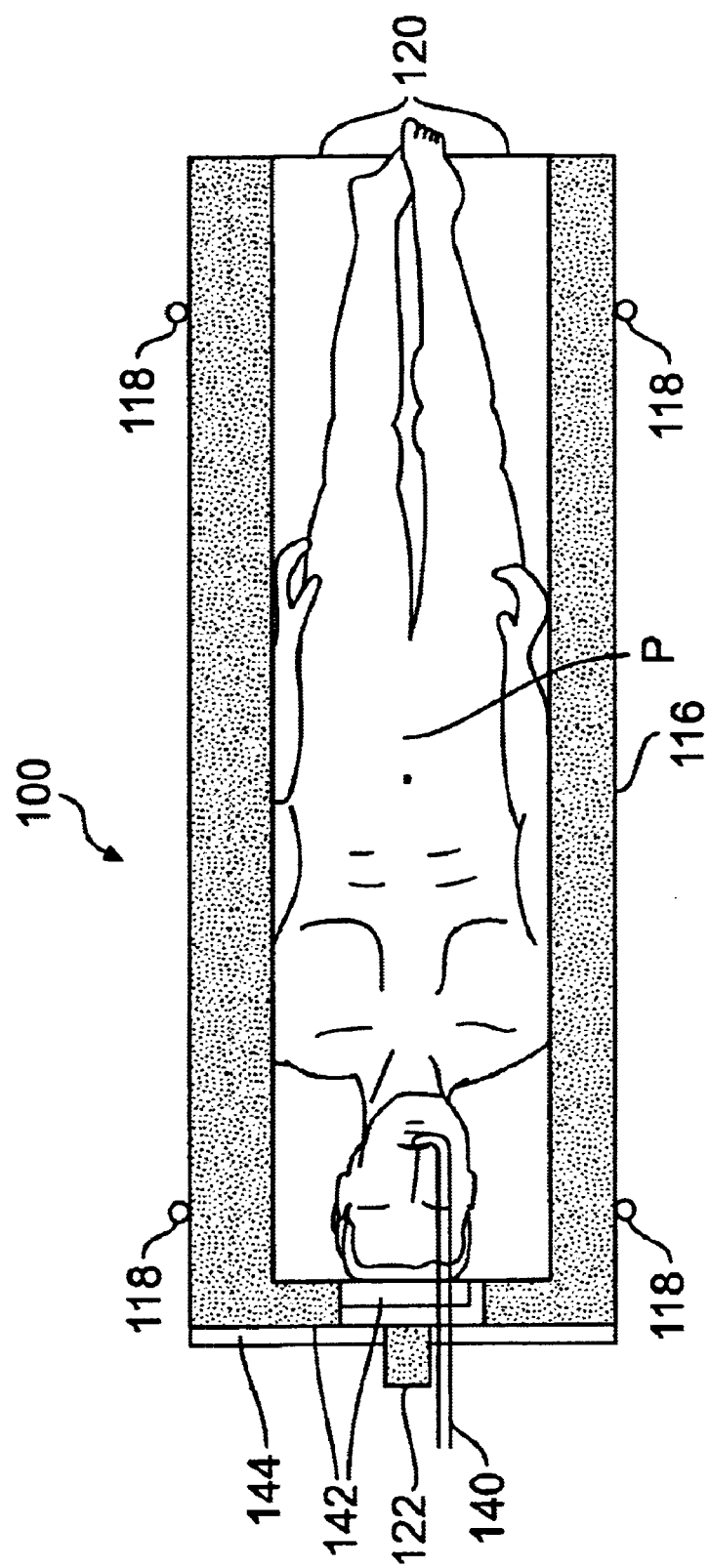

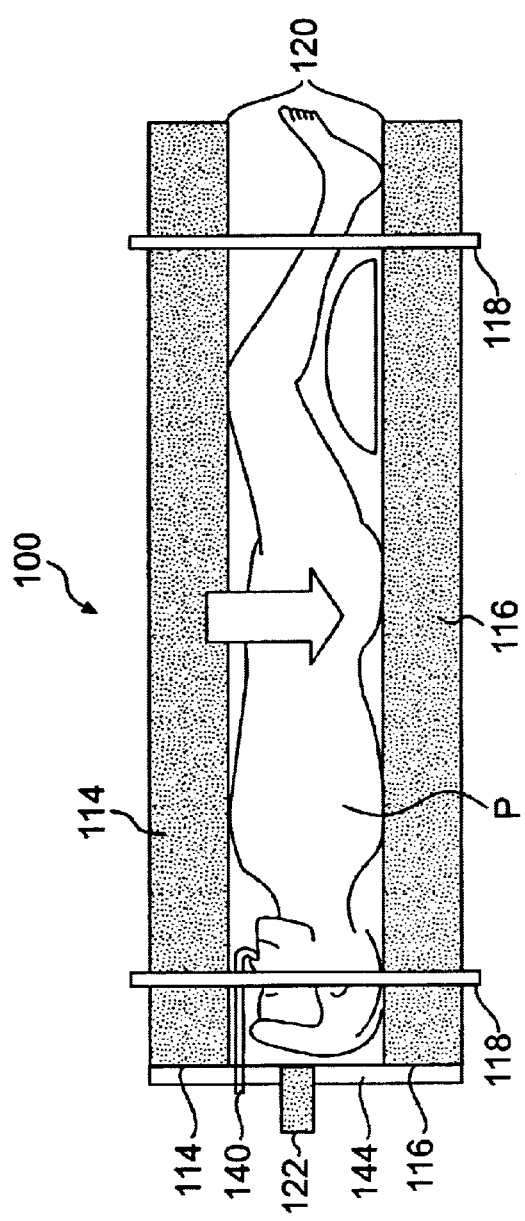
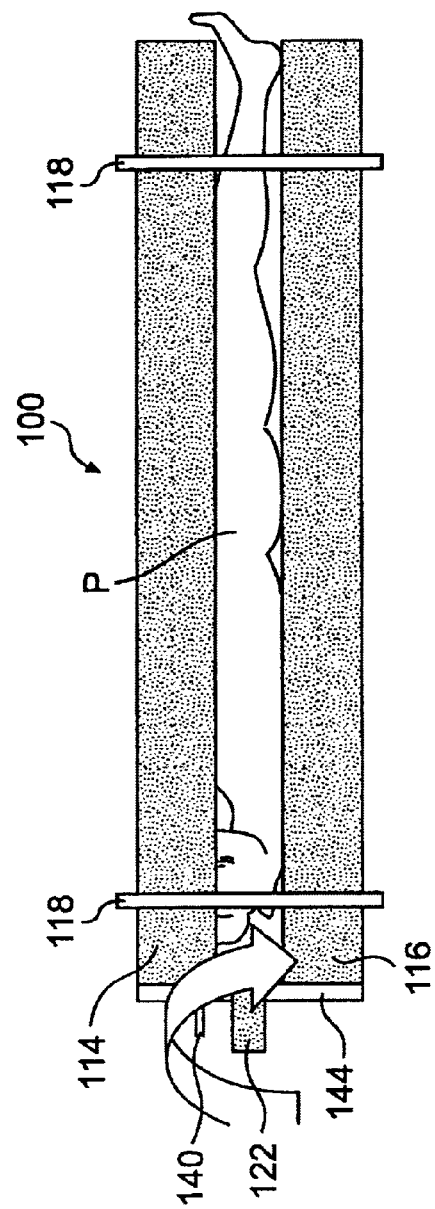

RADIOSURGERY METHODS THAT UTILIZE STEREOTACTIC METHODS TO PRECISELY DELIVER HIGH DOSAGES OF RADIATION ESPECIALLY TO THE SPINE

CROSS REFERENCE TO RELATED APPLICATION

This application claims benefit of priority from U.S. Provisional Ser. No. 60/194,589, filed Apr. 5, 2000, and is incorporated herein by reference in its entirety.

FIELD OF THE INVENTION

The invention provides novel methods for precisely delivering radiation to specific tissues and organ sites, especially the spine. In particular, the invention utilizes image-guided methods (stereotactic radiosurgery [SRS]) to deliver radiation to target sites, especially spinal metastases.

BACKGROUND OF THE INVENTION

Approximately 25,000 new patients present annually with metastatic tumors to the spine. With the aging population in the U.S. this number is expected to rise significantly over the next two decades. Of these, 60% of the metastases localize to the thoracic-spine, 30% to the lumbar-spine and 10% to the cervical-spine. The lesions cause pathological fracture, pain, deformity and compression of the neural axis or caudal equina. They may be single, but are more often multiple and scattered throughout several levels in different parts of the spine. Many of these patients are candidates for radiation therapy.

Conventional radiation therapy of these lesions involves the treatment of the spine, spinal cord and adjacent tissues. Tolerance doses have been established for the spinal cord at various levels [C-Spine (45–50 Gy) and T-Spine (40–45 Gy)] (based on reviews of clinical experiences). It is generally accepted that the radiation tolerance of blood vessels that supply the spinal cord play an integral role in this complex process. Therefore radio-surgical treatment planning may be designed to limit the radiation dose to the critical blood vessels that supply the spinal cord. FIG. 1 illustrates the locations and relevant positions of the relevant anatomical structures, including the aorta 10, spinal artery 12, intercostal artery 14, vertebral artery 16, medullary artery 18, nerve ganglion/root 20, thecal sac covering the spinal cord 22, Toly triangle 24, transverse process 26, spinous process 28, inferior facet 30, and superior facet 32.

Conventional radiation treatment delivery has several additional drawbacks. First, an excessive volume of otherwise normal hematopoeitic tissue (bone marrow) is irradiated, resulting in compromise of the patient's hematopoesis (ability to make new blood cells) and thus limiting further treatment options such as chemotherapy. Second, the time frame for delivery is excessive, and results in delays in systemic treatment (chemotherapy). Third, radiation cannot be administered over previously irradiated segments, nor immediately adjacent to previously irradiated segments.

OBJECTS OF THE INVENTION

An object of the invention is to alleviate the problems associated with conventional radiation oncology treatments. More specifically, the objects of the invention are: (a) to selectively deliver high dosages of radiation to specific sites near or contained in the spine, especially spinal metastases, by the use of image-guidance methods during radiotherapy; (b) to deliver high dosages of radiation to the spine while avoiding or minimizing the delivery of radiation to adjacent tissues, especially blood vessels in the Toly triangle; (c) to deliver a high single-fraction of radiation by stereotactic radiosurgery (SRS) to a target site, especially spinal metastases.

To achieve these objectives the invention provides an improved method for delivering therapeutic radiation to the spine comprising the following steps:

(i) immobilizing the spine with a novel immobilization bed;

(ii) obtaining a three-dimensional CT image of said immobilized patient which includes an area of the spine that is to be irradiated;

(iii) using said CT image to select an appropriate radiation dosage and volume and delivery protocol; and (iv) irradiating the spine of said patient according to said selected radiation and dosage protocol.

Preferably, the irradiating step (iv) will further be adjusted to the patient's respiratory cycle, i.e., by gating the radiation beam on and off at different points in the respiratory cycle.

BRIEF DESCRIPTION OF THE INVENTION

The present invention provides a novel and improved method for delivery of radiation to areas of the spine, e.g., spinal metastases, that allows for the precise delivery of high dosages of radiation while minimizing or avoiding the delivery of radiation to non-target sites, especially those comprised in the Toly triangle 24.

As discussed above, a significant problem associated with conventional radiation treatment of areas of the spine, especially tumors and metastases, is the fact that conventional delivery methods cannot deliver high dosages of radiation because of the risk of damage to non-target sites, especially critical blood vessels that are comprised in the Toly triangle 24. This is because such blood vessels are only tolerant to low dosages of radiation, e.g., on the order of 12–18 Gy.

This is a problem because low dosages of radiation, even if administered repeatedly, may be insufficient to eradicate the target, typically cancer cells. Also, conventional spinal radiotherapy typically requires a long time frame for delivery and response to radiation, and is moreover complicated by the fact that radiation cannot be administered over previously irradiated segments, nor immediately adjacent to previously irradiated segments of the spine.

The present invention alleviates all of said problems. In particular, the invention provides for the precise delivery of a high dosage of radiation to a target site or sites in the spine, that minimizes the exposure to non-target sites, such as the Toly triangle 24, and which can be effected during a relatively short period, i.e., by the use of stereotactic radiosurgery (SRS).

While the stereotactic radiosurgery technique has been utilized previously to treat intracranial lesions, heretofore it has not been applied to the spine and other extracranial lesions because of the inability to immobilize the spine and provide an accurate localization and three-dimensional planning target volume in a coordinated system that is suitable for both isodose planning and radiation treatment.

The present inventors have alleviated such problems by immobilization of the patient in a device which provides for the immobilization of the spine while a three-dimensional image (CT scan) of the spine is obtained. The CT images with specified coordinate system are utilized to determine appropriate radiation dosages and delivery (e.g., based on establishment of the isocenter and location of the target volume, and specification of target volume and critical structures), and further provide for precise alignment and immobilization of the patient as a therapeutic dosage of radiation is delivered by stereotactic radiosurgery (SRS).

In the present invention, the three-dimensional CT images will preferably be obtained by use of a mobile CT scanner which is set up such that the CT image can be transferred to a radiation treatment planning system that is used to determine optimal radiosurgery dosages and delivery. In preferred embodiments, this will be determined using appropriate software, i.e., BrainLab-Varian micro-MultiLeaf Collimator (mMLC), and the CT image will be obtained using the SpineLab Planar Fiducial system and the BrainLab ExacTrac System of IR markers and stereocameras.

This information will be utilized for inverse treatment planning for IMRT technique, which will take into account radiation sensitive structures, especially those within the Toly triangle. Radiosurgery is effected while the patient's spine remains immobilized and is precisely aligned in a suitable position for treatment, using the external coordinate system (ExacTrac) and SpineLab Planar Fiducial (SPF). During radiosurgery the radiation beam is preferably turned on/off or "gated" as a function of the respiratory cycle, in order to take into account natural fluctuations in a patient's position that occur during respiration.

BRIEF DESCRIPTION OF THE FIGS.

The present invention will be described with respect to the following drawing figures, in which like reference numerals will refer to like structures throughout the figures, and in which:

FIG. 2 is a top plan view of a patient in the supine position, the spine of which is immobilized in a cylinder-shaped cradle device according to the invention;

FIG. 3 is a side elevational view of a patient in the supine position in a cradle device according to the invention after the vertical lid of the cradle has been placed over the patient.

FIGS. 4 and 5 are side elevational views showing the cradle being rotated into the prone position, and the stabilization of the cradle with a lock pin or wedge;

Figure 8:
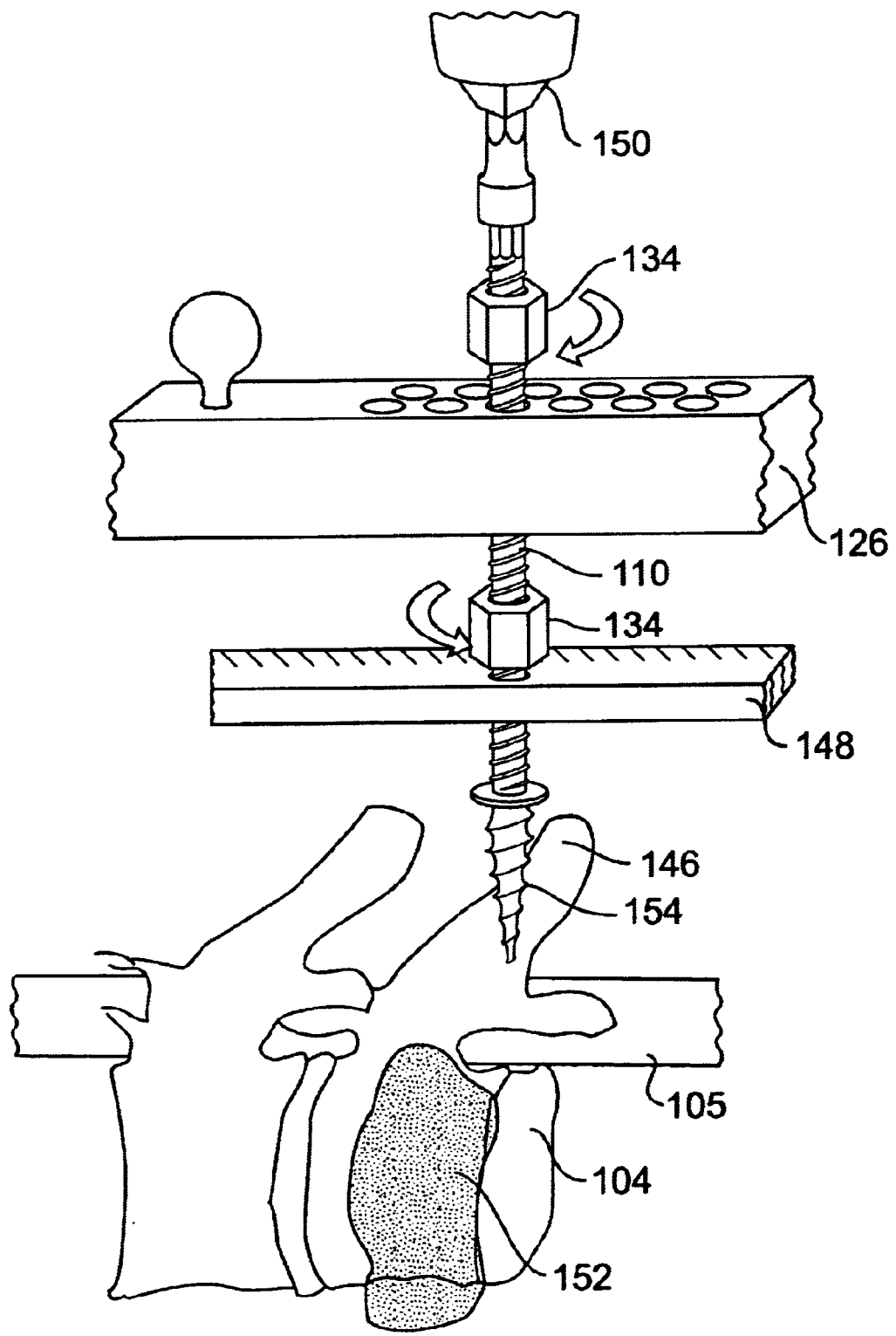
Figure 9A:
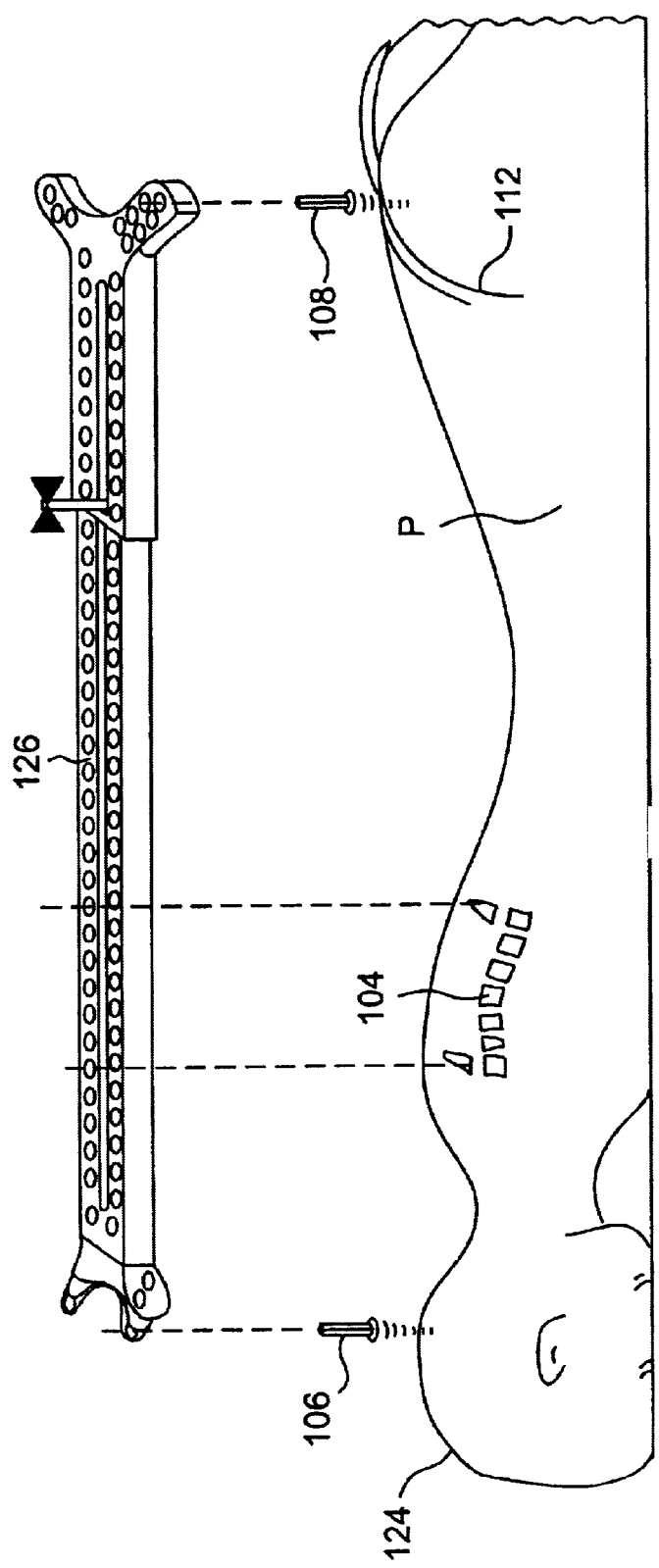
Figure 9B:
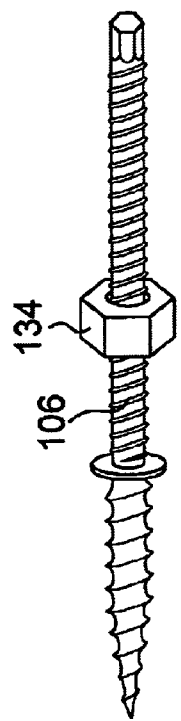

FIG. 8 is a perspective view illustrating the placement of spinelab planar fiducial (SPF) screws through the SPF and tightening nuts into selected vertebral levels and the tightening of the nuts over the SPF screws to firmly seat the SPF in relation to the spine, skull and iliac crest; and FIG. 9 is a side elevational view illustrating the placement of the SpineLab Planar Fiducial (SPF) over the cranial and iliac crest screws that allows for the adjustment of the SPF to a desired length of interposed spine, which area is to be treated by SRS according to the invention.

DETAILED DESCRIPTION OF THE INVENTION

The novel radiotherapeutic method of the invention comprises delivery by image-guidance of a high dosage of radiation to specific target sites in the spine by use of a novel immobilization device with stereotactic radiosurgery (SRS) technique. The present invention provides for the immobilization of the spine and accurate localization of the three-dimensional planning target volume in a coordinate system that is appropriate for both isodose planning and treatment.

According to the invention, a patient P is initially placed in a specially designed device that provides for the immobilization and localization of the patient's spine while CT imaging and SRS is effected.

The present invention provides for delivery of high doses of radiation to the spine by stereotactic radiosurgery SRS is an improvement over prior methods that involved application of external beam radiation to multiple segments of the spine. The present invention was made possible by design of a system that provides for the immobilization of the spine, accurate localization of the three-dimensional planning target volume, and a coordinate system that facilitates isodose planning and treatment set up.

Figure 1:
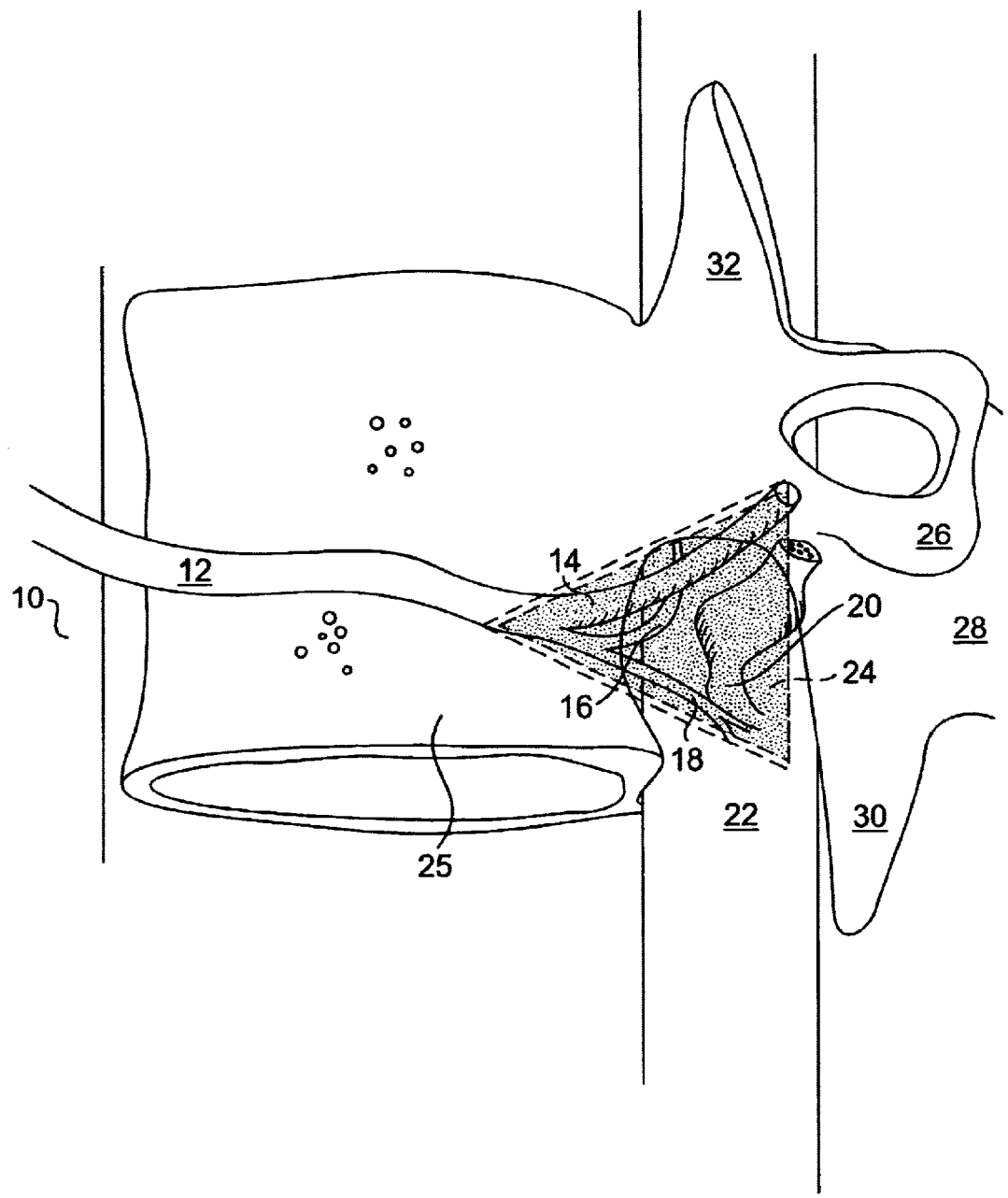
FIG. 1 is a schematic perspective view of the TOLY triangle; and surrounding anatomical structures.

The present invention delivers high dosages of radiation by a means that minimizes or avoids the delivery of radiation to non-target sites especially the critical blood vessels in the vascular triangle of the spinal vertebrae (Toly triangle 24, FIG. 1), where arteries supplying the spinal cord enter through the neural foramen. With respect thereto, these sensitive areas (vascular triangles) are found in the following levels of the spine:

$L_tC_1-L_4$ $R_tT_7-L_3$

The vertebrae foramina most likely to possess critical vascular structures are:

$L_tC_{2-3}$, $L_tC_{5-6}$, $L_tC_{7-1}$, bilateral $T_7$, $T_8$, $T_9$, $T_{10}$, $T_{11}$, $T_{12}$, $L_1$, $L_2$.

Therefore, the amount of radiation delivered thereto should be limited accordingly. Based thereon, patients with tumors within the posterior longitudinal ligament usually undergo surgical intervention. Therefore, the present invention delivers radiation to the spine by a manner that avoids injury to the bowel, kidneys, and peripheral nerves, and further avoids injury or loss of cells that are in adjacent vertebral levels which are involved in hematopoiesis and bone formation, as well as reducing risk of radiation induced transverse myelitis. Moreover, the present invention allows for rapid treatment, preferably a single dosage of radiation administered in a single treatment. By contrast, conventional methods require 20–30 daily treatments, posing unnecessary hardship to the patient as well as significantly raising costs associated with treatment.

Specifically, the use of stereotactic radiosurgery (SRS) during treatment of the spine allows for higher prescribed radiation dosages because of minimal irradiation of non-target (normal) tissues. Thereby, SRS provides for the treatment of tumor types which were previously considered radioresistant, such as metastatic chondrosarcomas, melanomas, and renal cell carcinomas.

The subject methods allow for delivery of precise dosages of radiation to specific sites. The use of SRS is advantageous in that it allows for doses to drop off by as much as 50–80% in a distance of 3 mm or less. This affords obvious advantages in that it allows for irradiation of spinal tumors or metastases that are positioned close to critical structures, such as spinal cord nerves and blood vessels which supply the spinal cord.

Radiosurgery involves the destruction of target tissues, e.g., tumors, by application of an intense beam of radiation. A necrotic dose is delivered to a tumor by cross-firing from several directions, in order to reduce the amount of energy deposited in healthy tissue. Therefore, in contrast to more invasive surgical techniques, tissue surrounding the tumor can be protected to some extent. Recently, radiosurgical methods have been improved because of computer models and apparatus that provide for high ablative accuracy. These improvements are the result of better focused radiation sources and imaging techniques.

However, notwithstanding such improvements, radiation necrosis of tissue adjacent to a treated tissue remains the major complication of stereotactic radiosurgery. Concerns remain as to whether particular volumes of tissue receive too much or too little radiation according to the prescribed treatment.

Radiosurgical treatment involves several steps. First, a precise three-dimensional (3D) map of the anatomical areas in the area of interest (herein the spine) is constructed using a computed tomography (CT) and/or magnetic resonance (MR) images. Next, the radiation beam pathways are computed to deliver a dose distribution that the oncologist and surgeon deem acceptable. Then, radiation beams are delivered by linear accelerators according to the planned treatment scheme.

A collimated radiation beam is then positioned according to the planned treatment scheme to deliver the radiation into a volume that closely conforms to the treatment volume, while avoiding exposure of healthy tissue. Systems and methods for performing stereotactic radiosurgery are known in the art and are disclosed, e.g., in U.S. Pat. No. 5,207,223, issued to Adler on May 4, 1993, and U.S. Pat. No. 5,458,125, issued Oct. 17, 1995 to Schweikard, which are incorporated by reference in their entirety herein.

The forward dosimetry problem involves computation of the dose distribution in a tissue given a treatment plan. (This essentially involves determination of tissue volumes to be treated and dosages of radiation.) The inverse dosimetry problem is to identify a treatment plan, the execution of which will achieve the desired dose distribution.

Dose distribution is an important parameter of radiosurgery. Whether fixed or frameless stereotactic radiosurgery is used, it is important to plan a particular scheme for the application of radiation beams to the tissue within prescribed limits such that damage to healthy tissues is minimized. This is especially important with present invention given the radiation sensitivity of areas such as the vascular Triangle 24 ("Toly Triangle").

The Schweikard patent identified above describes a treatment planning method and system for radiosurgery that includes apparatus that provides for up to six degrees of freedom, allowing full kinematic flexibility for manipulation of the radiation beam. Thus the beam can cross-fire from all directions at the tumor during treatment. Therein, a three-dimensional map of an anatomical area of interest is generated. Reverse planning comprises generating a sequence of beam configurations (positions and orientations) and radiation dose weight for achieving the specified distribution, particularly for non-spherical shapes.

In order to conform to the treatment targets, beam isocenter points are generated. The isocenters are selected based on the size and shape of the anatomical area of interest, e.g., a tumor. Radiosurgical treatment planning typically includes mapping a volume of tumorous tissue requiring irradiation and its surrounding areas to generate a model, distinguishing between tumor tissues and other (normal) regions, positioning isocenter points in a distributed manner within said model requiring irradiation, simulating radiation beams passing through said isocenter points, and determining which regions of the tumorous tissue received the predetermined doses of irradiation.

The present invention proposes to utilize similar methods for stereotactically delivery high radiation doses to the spine. As noted, the use of stereotactic radiosurgery has not been utilized in treating spinal tumors because of the lack of a system that provided for both immobilization of the spine and accurate three-dimensional planning target volume in a coordinate system that facilitates isodose planning and treatment setup. The protocol and system of the invention satisfies both of these goals.

Essentially, in the present invention, a patient P suspected or known to comprise a tumor or other tissue abnormality requiring radiation therapy is placed in a device 100 that provides for precise immobilization of the spine. A suitable device 100 according to the invention is shown in FIGS. 2 through 9. More specifically, FIG. 2 shows placement of a patient in a specially designed cylinder-shaped cradle 102 according to the invention in the supine position. It can be seen that this device 100 provides for immobilization of an area of the spine 104 using special screws 106, 108, 110, which are attached to a reference device 126 that precisely monitors a patient's position. More specifically, FIGS. 2–9 depict this apparatus 100 and also the attachment of a patient to a reference device 126 that allows for prior positioning of a patient P during computational tomography and administration of radiation.

This apparatus comprises a cradle having a dorsal and ventral side in which a patient is situated prior to attachment of the alignment device. In the figures, the following are identified:

P—patient
116—dorsal side cradle
140—endotracheal-tube
122—lockpin
118—fast release wing holes
120—pressurized cradle cushion
142—full length aperture between cushion
114—ventral side cradle
144—end plate
102—cradle
124—occiput
112—iliac crest
104—spine
126—spinelab planar fiducial (SPF)
106—occipital SPF screw
108—iliac crest SPF screw
110—spinous process SPF screw
146—spinous process
148—skin
150—screw driver
152—tumor in spine
105—spinal cord
154—penetration of screw into spinous process
134—zip nuts Concurrently or shortly after a patient is placed in such device, the patient is hooked up to IV lines that provide for the delivery of imaging materials, and the patient is anaesthetized, preferably by orotracheal or nasotracheal intubation. Also, the patient is preferably hooked up to a catheter that provides for the introduction of warming fluids that prevent hypothermia.

The patient P is administered a suitable imaging material, e.g., IV contrast, at a dosage suitable for imaging. Suitable dosages and materials are well known to those skilled in stereotactic radiosurgical methods.

Afterward, the anaesthetized patient is then restrained in the device by placement of the ventral lid 114 of the cradle 102 of the device 100 over the patient P. As can be seen from FIGS. 2 through 6, the exemplified device 100 has dorsal 116 and ventral 114 sides that cradle the patient. These sides are then tightened by appropriate fastening means. The exemplified cradle device is equipped with Ziplock® wing nuts 118 that allow for firm apposition of the dorsal 116 and ventral 114 sides on the cradle device 100 and restraint of the patient P therein as shown in FIG. 3. These fasteners are commercially available from Superior Products Inc., Cleveland, Ohio. These fasteners are equipped with a locking sleeve that prevents accidental disconnection during pressure and are resistant to loosening with vibration.

After the cradle device 102 is tightened, it is then pressurized to conform to the particular patient size and shape, while allowing for the patient's abdomen to remain free to permit proper respiration to be undisturbed. As can be seen from FIG. 2, the cradle includes pressurized cradle cushions 120.

Figure 5:
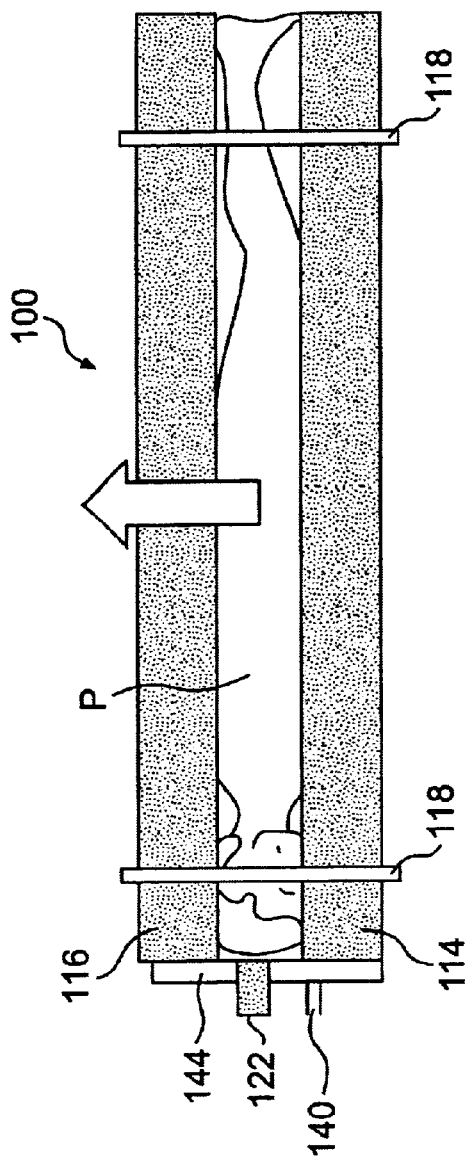
Figure 6:
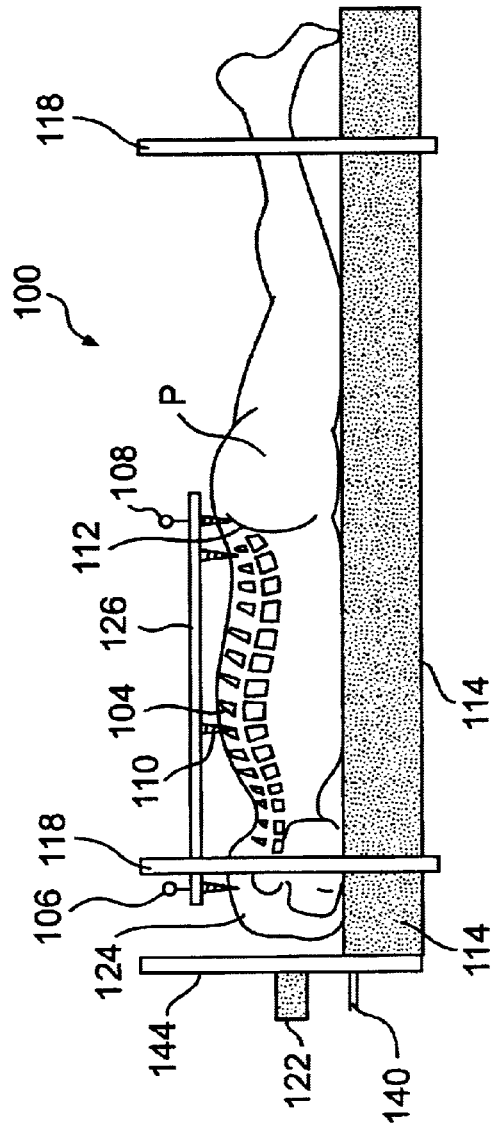
FIG. 6 is a side elevational a view of a patient immobilized in a cylinder-shaped cradle according to the invention, wherein the dorsal lid of the cradle has been removed to expose the back of a patient immobilized therein.

Afterward, the cradle 102 is then rotated so that the patient is lying in the prone position. This may be accomplished with a lockpin or wedge 122 as shown in FIGS. 4 and 5. Thereafter, the dorsal lid 116 of the cradle 102 is removed in order to expose the spinal area of the patient P as shown in FIG. 6. At that time, areas of the occipital skull, neck, back and hips are preferably sterilized, and the patient is preferably covered with clear plastic.

Figure 7:
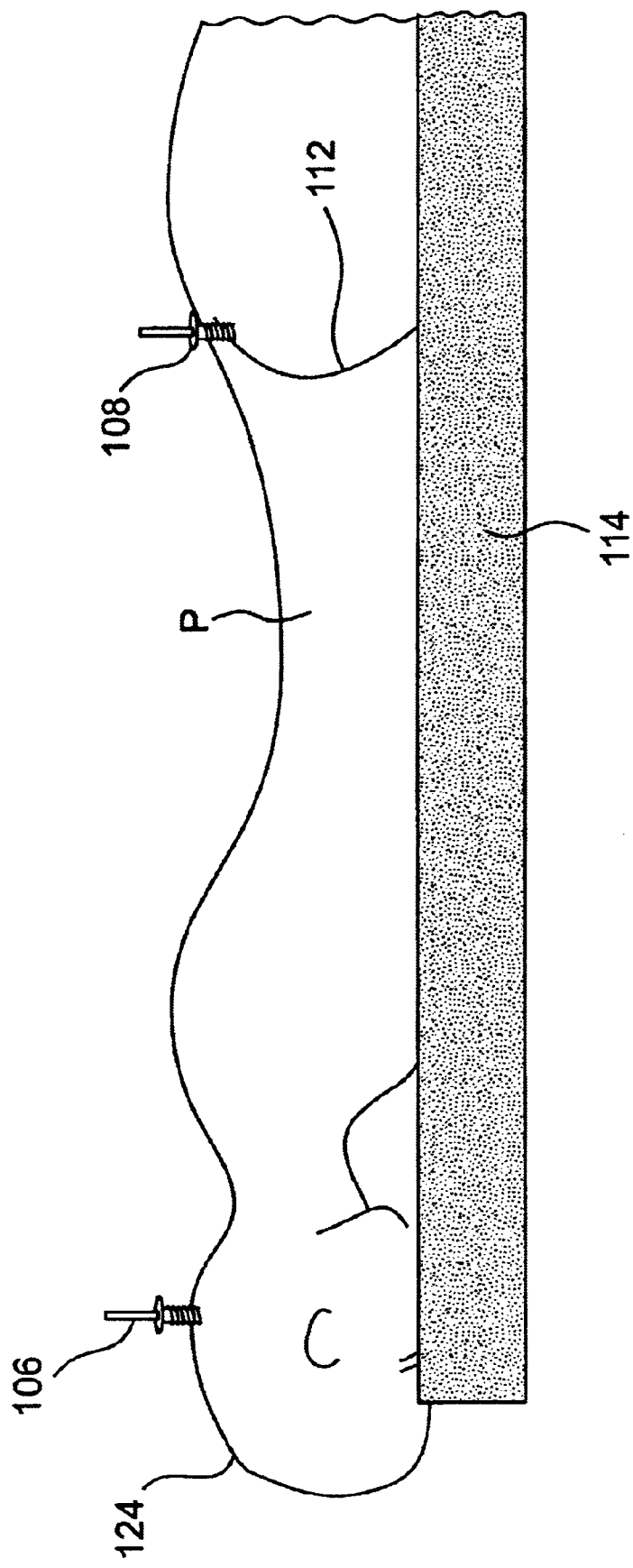
FIG. 7 is a dorsal view of a patient and depicts the placement of a cranial screw into the occipital skull and a cranial screw into the iliac crest.

Thereafter, spinal processes 26, 28 are identified by palpation, and vertebrae 25 in the vicinity are marked using fine needles. One or more cranial screws 106 are then placed into the occipital skull 124 and the iliac crests 112 as shown in FIG. 7. Suitable screws are commercially available and are known in the art. For example, U.S. Pat. No. 5,643,268 (incorporated by reference in its entirety herein) describes fixation pins for fixing a system for stereotactic treatment to bony structures, especially in the cranium. Essentially, these screws and pins 106, 108, 110 allow for placement of the reference device 126 that allows one to precisely monitor the patient's position.

After the pins 106, 108, 110 are placed, a suitable stereotactic reference system is then attached thereto. In the exemplified device, the SpineLab Planar Fiducial (SPF) 126 is placed over the cranial 106 and iliac screws 108, which are adjusted to the appropriate length of interposed spine 104, and the SPF 126 is locked down onto the screws 106, 108. As can be seen in FIGS. 6 and 8, screws 106, 108, 110 are placed through the SPF 126 and through tightening nuts 134 into selected vertebral levels, which are tightened to firmly seat and rigidly immobilize the SPF 126 relative to the spine 104, skull 124 and iliac crest 112.

Patient positioning, and the placement of the SPF 126, is not limited to the back of the patient. Alternative embodiments are anticipated. For instance, the patient may be positioned on the side or supine in a cradle. Immobilization devices or a SPF may be placed over the skull, chest and arterior iliac crests. The SPF therefore should be construed as an external reference system fixed to the patient, which assist in immobilizing the patient, and which provides fiducials which may be registered in a CT scanner or MRI for the purpose of localizing and/or verifying the location of the tumorous tissue within the body. The SPF may be designed for use with infrared cameras, such as Brainlab® (BrainLAB Med. Computersysteme GmbH, Poing, Germany) Exac Trac® system, or with wall-mounted stereocameras, such as the Accuray Cybernife® (Accuracy Inc., Santa Clara, Cali., United States) system.

The patient is then ready for CT scanning to establish appropriate radiosurgical regimen.

Suitable devices for CT scanning are well known. Preferably, a mobile CT scaner is used, e.g., available from Tomoscan M, Philips Medical System, Eindhoven, The Netherlands. This device has three components, the gantry, CT table, and operator's workstation. However, other CT scanning devices can be substituted therewith and are commercially available.

In this particular device, the gantry weights 460 kg and measures one meter deep, meters wide and two meters high. The aperture of the gantry is 60 cm with a maximal field of 46 cm. The gantry and the CT table of this particular device can translate 35 and 150 cm respectively.

The images produced by this device have a resolution of 512×512 pixels and can be transferred to other systems using the digital imaging and communications in medicine (DICOM) standard (National Electrical Manufactures Association, Rosslyn, Va., United States). As noted, this device is exemplary of Ct scanning devices which are commercially available for medical use.

Thereafter, scans of the target area will be obtained. In this regard, protocols for cervical, thoracic, and lumbar spine exist with slice thicknesses of 2, 3, 5 and 10 mm. Spinal CT scans can be reconstructed down to 1 mm. This system has a tube voltage of 130 KV, and uses a relatively low tube current between 10 and 50 mA, that minimizes dose expression.

An appropriate CT scanning procedure for spine radiosurgery will generate images in the target area that facilitate radiosurgery dose planning and delivery. The design of an appropriate CT protocol is within the purview of the ordinary medical artisan working in the area of CT scanning and radiosurgery.

In general, the procedure for CT scanning will include setting up the mobile CT scanner in the area that spinal radiosurgery is to be conducted, and positioning the patient such that CT scanning of the spinal area can be conducted. A spinal scan is then effected in the spinal region of interest, e.g., that allows for the reconstruction of 50 one-mm slides. This varies dependent on the size of the tumor or tumors that are to be irradiated.

CT images are obtained of the lesion or lesions (6) after placement of suitable IR markers and Infrared cameras. This is preferably effected by use of the SpineLab Planar Fiducial System and the BrainLab® ExacTrac® System of IR markers and stereocameras. This system is a computer controlled and integrated system that provides for precise patient positioning that includes two infrared cameras that enable precise tracking of reflective markers attached to the patient. This system allows for the capture of the three-dimensional positioning of a patient during simulation. The ExacTrac® System uses multiple markers distributed over the patient's body, placed at relatively immobile areas that do not move significantly (<3 mm) even with shallow breathing. The CT images are obtained, preferably at a specific phase of the respiratory cycle using a defined coordinate system. The CT images are viewed by an operator, and are transferred, e.g., via a network, to a system the designs the radiation treatment protocol based on the results contained in the CT scans. Preferably this is effected using the BrainLab-Varian Micro-MultiLeaf Collimator (mMLC).

Essentially, this comprises establishing the isocenter and location of target volume using the external reference (SPF frame) and markers (ExacTrac® localization markers). The target volume and critical structures will be specified by a neurosurgeon and/or radiation oncologist. Afterward, inverse treatment planning is selected based on the recommendation of a neurosurgeon and/or radiation oncologist. This treatment will take into account radiation sensitive structures such as are contained in the vascular triangle (FIG. 1), and prescribed dose limits. As noted, a significant advantage of the use of spinal SRS is that higher radiation dosages can be delivered relative to other methods of irradiating the spine without risk to non-target tissues.

For example, a prescribed dose limit may be 12 to 18 Gy or higher. Tolerance doses for the spinal cord at various levels have been established [(C-Spine (45–50 Gy) and T-Spine (40–45 Gy)]. The final treatment typically will be approved by a radiation oncologist.

Afterward, the patient will be precisely aligned for the SRS treatment protocol. Ideally, the position of the treated area will be aligned within 5 mm or lessso that the risk of irradiating a non-target site is negligible. More preferably, the treated spinal area will be aligned within about 3 mm of a desired position. Preferably, the patient will be placed prone on a linear accelerator treatment area (couch), and aligned for treatment based on an external coordinate system (e.g., ExacTrac® and SpineLab Planar Fiducial (SPF). Radiosurgery is then effected according to the suitable therapeutic protocol. Preferably, the radiation delivery system will include for respiratory gating of beam on/off, e.g. during usage of the mMLC.

As noted, the present invention affords significant advantages relative to conventional spine radiation treatments. In particular, it provides for high precision delivery of radiation, administration of higher radiation dosages, and convenience (patient can ideally be administered high level tumor-controlling or eradicating single dosage of radiation without risk to sensitive tissues.) This should minimize or prevent risk of radiation-induced myelitis, injury to bowel, kidneys, or peripheral nerves, and loss of bone marrow.

The present methods are suited for treating any condition wherein spinal radiotherapy or radiation of paraspinal tissues is therapeutically desirable. Such conditions include especially metastatic and primary bone tumors, spinal metastases, and is particularly suited for treatment of tumor types hitherto considered radioresistant.

EXAMPLE

Model Protocols According to the Invention

A. Induction, Positioning and Placement of Spinal Fiducials
1. Place the patient in the specially designed cradle in the supine position (FIG. 2).
2. Insert the I.V. lines.
3. Intubate the patient orotracheally or nasotracheally and induce the patient (anaesthesia); apply jet ventilation.
4. Place the Foley catheter, begin warming of the patient to prevent hypothermia
5. Administer the I.V. Contrast, double dose
6. Place the ventral lid of the cradle over the patient (FIG. 3)
7. Tighten the Ziplock®/wing nuts to firmly appose the dorsal and ventral cradles and restrain the anesthetized patient.
8. Pressurize (upper) ventral cradle, to conform to the patient habitues, allowing the Patient's abdomen to remain free (so as to allow normal diaphragmatic inspiration/expiration)
9. Rotate the cradle into the prone position, and stabilize the cradle with the lock pin or Wedge (FIGS. 4, 5)
10. Remove the dorsal lid of the cradle, exposing the back of the patient (FIG. 6)
11. Perform a sterile preparation of the occipital skull, neck, back and hips—drape the patient with clear plastic
12. Identify several spinous processes by palpation, mark several vertebrae in the vicinity with fine needles
13. Place one or two cranial screw(s) into the occipital skull, and one or more screws into the iliac crests (FIG. 7)
14. Place Spinelab Planar Fiducial (SPF) over the cranial and iliac crest screws, adjusting the SPF to the appropriate length of interposed spine. Lock down the SPF onto the screws to seat it firmly (FIG. 9)
15. Place the SPF screws through the SPF and through the tightening—nuts into selected vertebral levels; tighten the nuts over the SPF screws to firmly seat and rigidly immobilize the SPF in relation to the spine, skull and iliac crest (FIGS. 8 & 6)
16. CT scan the patient to establish precise intraoperative 3D registration of fiducials.

CT Imaging Technique

The mobile CT scanner (Tomoscan M, Philips Medical Systems, Eindhoven, The Netherlands) consists of three components: the gantry, the CT table, and the operator's workstation. The gantry weighs 460 kg and measures 1 meter deep, 2 meters wide, and 2 meters high. The aperture of the gantry is 60 cm with a maximal field of view of 46 cm. The gantry and the CT table can translate 35 cm and 150 cm, respectively. The images have a resolution of 512×512 pixels, and can be transferred to other systems using the digital imaging and communications in medicine (DICOM) standard. Protocols for cervical, thoracic, and lumbar spine exist with slice thickness options of 2, 3, 5, and 10 mm. Spiral CT scans can be reconstructed down to 1 mm. The system has a tube voltage of 130 kV, and uses a relatively low tube current between 10 and 50 mA, thereby minimizing dose exposure. Following is an outline of CT procedure for spine radiosurgery scanning:
1. Warm-up the mobile scanner in the spinal radiosurgery suite
2. Position the patient within the cradle in the prone position on table of the mobile CT scanner
3. Perform a spiral scan, and reconstruct approximately 50 one-mm slices, depending on the size the region of interest
4. Obtain the CT images of the lesion(s) using the Spinelab Planar Fiducial system and the BrainLab® ExacTrac® system of IR markers and stereo-cameras. By this means localise the patient and lesion(s) (probably at a specific phase of the respiratory cycle) in a defined coordinates system
5. View the images on the CT operator's workstation
6. Transfer the scans to the Brainlab dose planning software via the network.

C. Treatment Planning and Delivery Technique
1. Transfer the CT-image set to a radiation treatment planning system for radiosurgery dose planning and delivery based on using the BrainLab-Varian micro-MultiLeaf Collimator (MMLC)

2. Establish the isocenter and location of the target volume using the external reference SPF frame and the Exac Trac localization markers
3. Specify the target volume and critical structures as outlined by Neurosurgeon and Radiation Oncologist
4. Perform an inverse treatment planning for IMRT treatment technique based on the input from the Neurosurgeon and Radiation Oncologist (e.g. Prescribed dose limit 12 to 18 Gy, special accommodation for radiation sensitive structures within the Toly Triangle 24
5. Identify the final treatment delivery plan as approved by Radiation Oncologist
6. Place the patient prone in the cradle on the linear accelerator treatment couch
7. Set-up and align the patient into treatment position based on the external coordinate system (ExacTrac®) and Spinelab Planar Fiducial (SPF)
8. Deliver radiosurgery, with possible respiratory gating of beam on/off, using the MMLC

What is claimed is:

1. A method for delivery of a therapeutic dosage of radiation to a target site near the spine comprising the following steps:
    (i) immobilizing the area of the spine of a patient that includes a target site that is to be treated using stereotactic radiosurgery, wherein said immobilizing comprises placing one or more fasteners in a first anatomical structure in or adjacent to the spine, and placing one or more fasteners in a second anatomical structure in or adjacent to the spine;
    (ii) obtaining CT images of said area of the spine;
    (iii) using said images to identify a target volume and areas that are to be protected from irradiation;
    (iv) designing a stereotactic radiotherapeutic protocol based on the identified target volume and critical structure; and
    (v) precisely aligning said patient in a determined position suitable for effecting said radiotherapeutic protocol; and
    (vi) effecting said stereotactic radiosurgery protocol.

2. The method of claim 1, wherein said immobilizing comprises using a device that includes the placement of one or more screws in the cranium and one or more screws in the iliac crest between a length of interposed spine including the target site.

3. The method of claim 2, wherein said screws are attached to a reference system for stereotactic radiation treatment.

4. The method of claim 3, wherein said reference system comprises a planar fiducial reference system.

5. The method of claim 3, wherein said system includes infrared markers that allow for the precise positioning of the patient.

6. The method of claim 5, wherein said system includes infrared cameras.

7. The method of claim 1, wherein step (ii) comprises performing a spinal scan of a targeted area of the spine.

8. The method of claim 1, wherein step (ii) is effected at a specific phase of the respiratory cycle, or wherein step (ii) is effected whilst the patient is intubated and undergoing "jet ventilation."

9. The method of claim 1, wherein said stereotactic radiosurgery protocol includes respiratory gating of beam on or off during specific times of the respiratory cycle.

10. The method of claim 1, wherein said delivery spares the Toly vascular triangle.

11. A method of treating a spinal tumor or metastasis, comprising administering the method of claim 1.

12. A method of treating a radioresistant cancer, comprising administering the method of claim 1.

13. The method of claim 12, wherein said cancer is chordoma, chondrosarcoma, melanoma or renal cell carcinoma.

14. A system for effecting spinal stereotactic radiosurgery (SRS) that comprises the following:
    (i) a device that provides for the precise positioning and immobilization of the spine of a patient that is to be treated by SRS by placement of one or more fasteners in a first anatomical structure in or adjacent to the spine, and placement of one or more fasteners in a second anatomical structure in or adjacent to the spine;
    (ii) an SRS reference system constructed and arranged to be coupled to said fasteners for precise determination of the position and alignment of the patient;
    (iii) a CT scanning device that provides for the generation of CT images of a predetermined area of the immobilized spine of said patient;
    (iv) a means for transferring said CT images to a radiation planning system that includes computer software that designs an appropriate SRS protocol based on said CT images; and
    (v) means for effecting said SRS protocol.

15. The system of claim 14, wherein said SRS reference system comprises a planar fiducial reference system.

* * * * *